United States Patent
Melby et al.

(10) Patent No.: US 6,180,576 B1
(45) Date of Patent: Jan. 30, 2001

(54) CONDITIONING SHAMPOO COMPOSITIONS

(76) Inventors: Allan L. Melby, 104 Heathercroft Dr., Cranberry Township, PA (US) 16066; Gary F. Matz, 207 Alden Rd., Carnegie, PA (US) 15106

(*) Notice: Under 35 U.S.C. 154(b), the term of this patent shall be extended for 0 days.

(21) Appl. No.: 09/136,840

(22) Filed: Aug. 20, 1998

(51) Int. Cl.⁷ ................. C11D 3/37; C11D 3/22
(52) U.S. Cl. ............ 510/121; 510/123; 510/125; 510/466; 510/476; 424/70.11; 424/70.12; 424/49
(58) Field of Search ............ 424/70.11, 70.12, 424/401; 510/121, 123, 125, 466, 476

(56) References Cited

U.S. PATENT DOCUMENTS

| | | |
|---|---|---|
| 2,826,551 | 3/1958 | Geen .............................. 91/1 |
| 3,964,500 | 6/1976 | Drakoff ........................... 132/7 |
| 4,364,837 | 12/1982 | Pader ............................... 252/173 |
| 4,741,855 | 5/1988 | Grote et al. ..................... 252/142 |
| 4,788,065 | 11/1988 | Nakamura et al. . | |
| 5,573,709 | 11/1996 | Wells . | |
| 5,587,154 | * 12/1996 | Dowell et al. .................. 424/70.11 |
| 5,972,356 | * 10/1999 | Peffly et al. ..................... 424/401 |
| 5,980,877 | * 11/1999 | Baravetto et al. .............. 424/70.11 |
| 5,985,294 | * 11/1999 | Peffly .............................. 424/401 |

FOREIGN PATENT DOCUMENTS

| | | |
|---|---|---|
| 0413416A2 | 2/1991 | (EP) . |
| 849433 | 9/1960 | (GB) . |
| 93/08787 | * 5/1993 | (WO) . |
| WO93/08787 | 5/1993 | (WO) . |

OTHER PUBLICATIONS

Japanese Abstract 53[1978]–35902 (54129135), Accession No. 79–83353B/46, Mar. 28, 1978.
Japanese Abstract 62[1987]–327266 (168612), Accession No. 89–232269/32, Dec. 25, 1987.
Japanese Abstract 56072095, Accession No. 1981:592207, 19810616.

* cited by examiner

Primary Examiner—Kery Fries

(57) ABSTRACT

A hair conditioning shampoo composition is disclosed that contains (a) a surfactant component that can contain anionic surfactants and/or amphoteric surfactants (optionally including zwitterionic and nonionic surfactants), (b) a dispersed, insoluble, nonionic silicone hair conditioning agent, (c) a water soluble, organic, ampholytic polymer hair conditioning agent; and (d) an aqueous carrier. The conditioning shampoo composition optionally contains an organic, water insoluble, liquid.

15 Claims, No Drawings

CONDITIONING SHAMPOO COMPOSITIONS

FIELD OF THE INVENTION

The present invention relates to shampoo compositions containing surfactant and conditioning ingredients. The present invention also relates to methods for treating hair.

BACKGROUND OF THE INVENTION

Clean human hair quickly returns to its "dirty" condition due to contact with the environment and due to the buildup of the sebum-secreted by the head. Within a short time (one day to a few days) hair begins to look and feel "dirty". In modern cultures, this look and feel is considered unacceptable requiring the wearer to shampoo their hair frequently. In some countries, the daily shampooing of hair is considered a normal requirement for proper hygiene, whether or not the hair has actually become "dirty".

Shampooing cleans the hair by the removal of environmental contaminants along with the sebum. However, shampooing removes the natural oils and other moisturizing materials. If the hair is of significant length, the hair can be tangled and becomes unmanageable. Once dry, the hair has lost its shine and luster and can be dry and frizzy. Hair can also maintain a static charge when dry that results in "fly-away hair".

As this problem has surfaced in the modern era, solutions have been developed to correct or to minimize the problem from frequent shampooing. The first acceptable solutions entailed the post-shampoo application of hair conditioners and hair rinses, generally while the hair is still wet immediately after shampooing. These conditioners and rinses were left on the hair for a period of time to allow sufficient treatment and then removed by rinsing with water. These solutions have, as late, been deemed inconvenient and time consuming. The solution to this problem has been the incorporation of conditioners into the shampoo itself, thus the advent of "conditioning shampoo".

Shampoos that contain conditioners or conditioning agents have not been completely satisfactory for various reasons. Hair is composed of keratin, a sulfur-containing fibrous protein. The isoelectric point of keratin, and more specifically of hair, is generally in the pH range of 3.24.0. Therefore, at the pH of a typical shampoo (about 5.5–6.5), hair carries a net negative charge. Consequently, cationic polymers due to their positive charge have long been used as conditioners in shampoo formulations, or as a separate treatment, in order to improve the wet and dry combability of the hair. The substantivity of the cationic polymers for negatively charged hair along with film formation facilitates detangling during wet hair combing and a reduction in static flyaway during dry hair combing. Cationic polymers generally also impart softness and suppleness to hair.

When cationic polymers are added to shampoos containing good cleaning anionic surfactants, formation of highly surface active association complexes generally takes place, which imparts improved foam stability to the shampoo but provides poor conditioning. Maximum surface activity and foam stability, or lather, are achieved at near stoichiometric ratios of anionic surfactant: cationic polymer, where the complex is least water soluble. However, cationic conditioners exhibit some incompatibility at these ratios. Compatibility gives a commercially more desirable clear formulation, while incompatibility leads to a haze or precipitation, which is aesthetically less desirable in some formulations. Additionally when cationic surfactants are added as an ingredient in the shampoo, they do not provide optimal overall conditioning to the hair in the area of softness and tend to build up on the hair resulting in an unclean feel.

Nonionic silicones have also been disclosed in patents as a shampoo additive to increase the softness of hair. These patents include U.S. Pat. Nos. 2,826,551, 3,964,500, 4,364,837, and U.K. Patent No. 849,433. Shampoo compositions that contain insoluble silicone conditioners are disclosed in U.S. Pat. Nos. 4,741,855 and 4,788,066. Shampoo compositions containing anionic surfactants dispersed in soluble silicone (along with a cationic polymer with a cationic charge density of 3 meq/k or less and an oily liquid conditioning agent) are disclosed in WO93/08787 and in U.S. Pat. No. 5,573,709.

Other publications disclosing the use of silicone conditioning agents include Japanese Patent Application No. 5672095, Laid Open Jun. 16, 1981, published EPO Application 413 416 and 413 417, both published Feb. 20, 1991.

Oily components have been added to shampoo formulations to improve the luster and shine of hair as disclosed in Japanese Patent Application Abstracts 53[1978]-35902, (54129135) and 62[1987]-327266 (168612).

In spite of these attempts to provide optimal combinations of cleaning ability and hair conditioning, it remains desirable to provide further improved hair conditioning shampoo compositions. For instance, it remains desirable to improve overall conditioning, and especially shine and luster, wet and dry combing, and dry hair feel, of hair treated with shampoo containing silicone and cationic material. For shampoos containing oily materials in combination with cationic materials, it remains desirable to improve overall conditioning:, especially wet combing and detangling, dry combing, and dry hair feel. However merely increasing the level of one or both conditioning ingredients can result in adverse effects such as greasy hair feel and loss of fullness. It is desirable to improve conditioning without suffering from these drawbacks.

It is desirable to provide shampoo compositions and methods for cleaning and conditioning hair which can provide excellent cleaning performance and improved levels of conditioning while minimizing any adverse side effects associated with build-up due to the use of excess conditioning agent.

SUMMARY OF THE INVENTION

The hair conditioning shampoo composition of the present invention comprises:
(a) about 5% to about 50%, by weight, of a surfactant component selected from the group consisting of anionic surfactants and amphoteric surfactants;
(b) about 0.05% to about 10%, by weight, of a dispersed, insoluble, nonvolatile, nonionic silicone hair conditioning agent;
(c) about 0.05% to about 10%, by weight, of a water soluble, organic, ampholytic polymer hair conditioning agent; and
(d) an aqueous carrier.

The method for treating hair according to the present invention comprises contacting the hair with the composition above.

DETAILED DESCRIPTION OF THE INVENTION

This invention provides anionic and/or amphoteric detersive surfactant containing liquid shampoo compositions that can provide both excellent cleaning performance and hair conditioning benefits to a wide variety of hair types. This is attained by forming a hair conditioning system shampoo composition that includes the surfactant, an aqueous carrier, a dispersed insoluble, nonionic, silicone hair conditioning agent, a water soluble, organic ampholytic polymer hair conditioning agent, and optionally, an organic, water insoluble oily liquid.

It has now been unexpectedly found that improved overall conditioning can be found by combining surfactant in a shampoo with dispersed, insoluble, and nonionic silicone, a soluble organic ampholytic polymer hair conditioning agent. Conditioning is also improved with the addition of a preferred optional organic water insoluble liquid component.

These compositions can provide improved conditioning while reducing the level of undesirable side effects that can result from increasing the level of conditioning agent in prior known conditioning systems. As discussed previously, a conditioning agent system containing too much of a particular component can cause buildup. Too much silicone can result in silicone build up on the hair over repeated usage and a loss of fullness of the hair. Too much organic liquid (oil) results in an oily feel and a loss of fullness of the hair. Too much conditioning agent results in a slick, oily feel of the hair. Now it has been found that combining these specific types of ingredients—surfactant, insoluble nonionic silicones, ampholytic polymers, and the optional oily organic liquids—can provide improved overall conditioning while minimizing the adverse effects of conditioning agent build-up that otherwise can be incurred upon increasing the levels of individual components in prior known conditioning systems. Furthermore, the use of ampholytic polymer in the compositions hereof can improve performance relative to similar systems with cationic polymers in combination with silicone and oily liquid conditioning agents.

The present invention provides hair conditioning shampoo compositions comprising: about 5% to about 50%, by weight, of component (a), about 0.05%. to about 10%, by weight, of component (b); about 0.05% to about 10%, by weight, of component (c); and an aqueous carrier (d). The hair conditioning shampoo compositions preferably contain about 0.05% to about 5%, by weight, of an organic, water insoluble, liquid that is more preferably selected from the group consisting of hydrocarbon oils, fatty esters having 10 or more carbon atoms, and mixtures thereof. The hair conditioning shampoo compositions can also contain from 0% to about 10%, by weight, of a zwitterionic surfactant component.

A specific preferred composition according to the present invention comprises; (a) containing about 15 weight % anionic surfactant and about 1 to 2 weight % nonionic surfactant, (b) containing about 0.5 to 1.5% silicone, and (c) containing about 0.2 to 0.4 weight percent of said ampholytic polymer hair conditioning agent.

The optional organic water insoluble liquid is an oily liquid conditioning agent and is preferably intermixed in, and is distributed throughout, the composition. The organic water insoluble liquid is generally selected from the group consisting of hydrocarbon oils and fatty esters. As used herein, "fatty ester" means esters having 10 or more carbon atoms.

The insoluble silicone conditioning agent is dispersed throughout the composition in the form of droplets or particles. Preferably, a suitable suspending agent is utilized to facilitate stability of the dispersed silicone.

As used herein, the terms "soluble" and "insoluble" used in reference to particular ingredients of the shampoo compositions refer to solubility or insolubility, respectively, of that ingredient in the shampoo composition, unless otherwise specifically indicated. For example the terms "water soluble" and "water insoluble", as used herein, refer to solubility of the particular ingredient in water, as opposed to solubility in the shampoo composition.

All percentages are calculated by weight of the total composition unless otherwise specifically indicated. All ratios are weight ratios unless otherwise specifically indicated.

Ampholytic Polymer Hair Conditioning Agent

The shampoo composition of the present invention comprises a water soluble, ampholytic organic polymer hair conditioning agent as an essential element. The polymeric ampholytic hair conditioning agent hereof will generally be present at levels of from about 0.05% to about 10% by weight preferably about 0.05% to about 5%, more preferably from about 0.1% to about 4%, with about 0.2% to about 3%, by weight, of the shampoo composition being most preferred. By "water soluble" ampholytic organic polymer, what is meant is a polymer which is sufficiently soluble in water to form a substantially clear solution to the naked eye at a concentration of 0.1% in water (distilled or equivalent) at 25° C. Preferably, the polymer will be sufficiently soluble to form a substantially clear solution at 0.5% concentration, more preferably at 1.0% concentration.

The ampholytic organic polymers useful in the hair conditioning agent hereof are organic polymers that can provide conditioning benefits to hair and that are soluble in the shampoo composition. Any ampholytic polymers which can provide these benefits can be used regardless of the cationic charge density of the polymer.

The water soluble, organic, hair conditioning agent of the ampholytic polymer hair conditioning shampoo composition according the present invention is preferably comprised of:

(A) about 1 to about 99 mol % of at least one monomer selected from the group consisting of alkyl acrylamidopropyl-dimethyl ammonium halides, alkyl methacrylamidopropyldimethyl ammonium halides, alkyl acryloyloxyethyl dimethyl ammonium halides, alkyl methacryloyloxyethyl dimethyl ammonium halides, and dialkyl diallyl ammonium halides;

(B) about 1 to about 99 mol % of at least one monomer selected from the group consisting of acrylic acid (AA), methacrylic acid (MAA), 2-acrylamido-2-methylpropane sulfonic acid (AMPSA) 2-methacrylamido-2-methylpropane sulfonic acid (MAMPSA), n-methacrylamidopropyl,n,n-dimethyl,amino acetic acid, n-acrylamidopropyl,n,n-dimethyl,amino acetic acid, n-methacryloyloxyethyl,n,n-dimethyl,amino acetic acid, and n-acryloyloxyethyl,n,n-dimethyl,amino acetic acid; and (C) about 0 to about 80 mol % of at least one monomer selected from the group consisting of $C_1$–$C_{22}$ straight or branched chain alkyl acrylate or methacrylate, a $C_1$–$C_{22}$ straight or branched chain n-alkyl acrylamide or methacrylamide, acrylamide methylacrylamide, n-vinylpyrrolidone, vinyl acetate or ethoxylated and propoxylated acrylate or methacrylate; with a weight average molecular weight of, as determined by viscometry, of at least about 50,000.

The water soluble, organic, ampholytic polymer hair conditioning agents of the present invention are organic polymers which more preferably comprise:

(A) acrylamidopropyltrimethyl ammonium chloride (APTAC), methacrylamidopropyltrimethyl ammonium chloride (MAPTAC), acryloyloxyethyl trimethyl ammonium chloride (AETAC), methacryloyloxyethyl methyl sulfate (METAMS), methacryloyloxyethyl trimethyl ammonium chloride (METAC), or dimethyl diallyl ammonium chloride (DMDAAC);

(B) AA, MAA, AMPSA, and MAMPSA; and (C) optionally, a $C_1$–$C_{22}$ straight or branched alkyl acrylate or methacrylate, such as methyl, ethyl, butyl, octyl, lauryl, and stearyl acrylate esters, and methacrylate esters; acrylamide;

methacrylamide; a $C_1$–$C_{22}$ straight or branched n-alkyl acrylamide or methacrylamide such as n-methyl, n-ethyl, n-butyl, n-octyl, t-octyl, n-lauryl, and n-stearyl acrylamides and methacrylamides.

The shampoo composition has a pH preferably between about pH 3 and about pH 9, more preferably from about pH 4 to about pH 8.

Preferably, the mol ratio of (A):(B) in said ampholytic polymer ranges from about 20:80 to about 95:5, more preferably from about 25:75 to about 75:25. Further, the weight average molecular weight of said polymer, as determined by viscometry, is preferably at least about 100,000, more preferably from about 100,000 to about 10,000,000, with a weight average molecular weight of about 200,000 to about 8,000,000 being most preferred. Alternatively, gel permeation chromatography (GPC) with light scattering detection can be used with approximately the same numbers.

Optionally, but preferably, the instant polymers additionally contain, are further comprised of or are prepared using (C) up to about 80 mol percent, preferably at least about 0.1 mol percent, of a $C_1$–$C_{22}$ straight or branched chain alkyl acrylate or methacrylate, preferably a $C_1$–$C_4$ alkyl acrylate and most preferably methyl acrylate, a $C_1$–$C_{22}$ straight or branched chain n-alkyl acrylamide or methacrylamide, preferably a $C_1$–$C_4$ alkyl acrylamide and most preferably acrylamide, wherein the upper mol percent of (C) in the instant polymers is limited by solubility considerations.

A more preferred molecular weight range for the instant polymers is from about 200,000 to about 8,000,000, as determined by viscosity or GPC. For example, reduced viscosity values can be used to approximate the weight average molecular weights of the instant polymers. Preferably, the mol ratio of (A):(B) ranges from 25:75 to about 75:25, and the preferred polymers contain at least about 0.1 up to about 20 mol % of the above-defined acrylates, methacrylates, acrylamides, methacrylamides, vinyl acetate, vinyl alcohol and/or n-vinyl pyrrolidone. More preferably, the instant polymers contain about 5 to about 15 mol % of the acrylate, methacrylate, acrylamide, methacrylamide, vinyl acetate, vinyl alcohol and/or n-vinyl pyrrolidone moiety. In the most preferred case, methyl acrylate and/or acrylamide.

Specific preferred examples of the ampholytic polymer hair conditioning agent according to the present invention include (1) a polymer comprised of about 45 mol % MAPTAC, about 45 mol % acrylic acid, and about 10 mol % methylacrylate and (2) a polymer comprised of about 30 mol % DMDAAC, about 35 mol % acrylic acid, and about 35 mol % acrylamide. These polymers are available from Calgon Corporation as MERQUAT 2001 and MERQUAT plus 3330, respectively.

As discussed above, the ampholytic polymer hereof is water soluble. This does not mean, however. that it must be soluble in the shampoo composition. Preferably however, the ampholytic polymer is either soluble in the shampoo composition, or in a complex coacervate phase in the shampoo composition formed by the ampholytic polymer and other ionic materials. Complex coacervates of the ampholytic polymer can be formed with anionic surfactants, amphoteric surfactants, zwitterionic surfactants, cationic surfactants or with appropriately charged polyelectrolytes that can optionally be added to the compositions hereof.

Coacervate formation is dependent upon a variety of criteria such as molecular weight, concentration, and ratio of interacting ionic materials, ionic strength (including modification of ionic strength, for example, by addition of salts), charge density of the cationic and anionic species, pH, and temperature. Coacervate systems and the effect of these parameters has previously been studied. See, far example, J. Caelles, et al) "Anionic and Cationic Compounds in Mixed Systems", *Cosmetics & Toiletries,* Vol. 106, April 1991, pp. 49–54, C. J. van Oss, "Coacervation, Complex Coacervation and Flocculation", *J. Dispersion Science and Technology,* Vol. 9 (5,6), 1988–89, pp. 561–573, and D. J. Burgess, "Practical Analysis of Complex Coacervate Systems", *J. of Colloid and Interface Science,* Vol.: 140, No. 1, November 1990, pp. 227–238.

It is believed to be particularly advantageous for the ampholytic polymer to be present in the shampoo in a coacervate phase, or to form a coacervate phase upon application or rinsing of the shampoo to or from the hair. Complex coacervates are believed to more readily deposit on the hair. Thus, in general, it is preferred that the ampholytic polymer exist in the shampoo as a coacervate phase or form a coacervate phase upon dilution. If not already a coacervate in the shampoo, the ampholytic polymer will preferably exist in a complex coacervate form in the shampoo upon dilution with water to a water:shampoo composition weight ratio of about 20:1, more preferably at about 10:1, even more preferably at about 8:1.

Techniques for analysis of formation of complex coacervates are known in the art. For example, microscopic analyses of the shampoo compositions, at any chosen stage of dilution, can be utilized to identify whether a coacervate phase has formed. Such coacervate phase will be identifiable as an additional emulsified phase in the composition. The use of dyes can aid in distinguishing the coacervate phase from other insoluble phases dispersed in the composition.

Exemplary complex coacervate shampoo compositions are shown in the examples.

Anionic Surfactant

The hair conditioning shampoo compositions of the present invention preferably contains an anionic surfactant as at least part of component (a), which can comprise one or more anionic detersive surfactants which are anionic at the pH of the shampoo, to provide cleaning performance to the composition.

The anionic surfactant of component (a) can be the only surfactant and will generally be present at a level from about 5% to about 50%, preferably from about 8% to about 30%, more preferably from about 10% to about 25%, of the composition, with about 15% being most preferred.

Anionic detersive surfactants useful herein include those that are disclosed in U.S. Pat. No. 5,573,709, the disclosure of which is incorporated herein by reference in its entirety. Examples include alkyl and alkyl ether sulfates. Specific examples of alkyl ether sulfates which may be used In the present invention are sodium and ammonium salts of lauryl sulfate, lauryl ether sulfate, coconut alkyl triethylene glycol ether sulfate; tallow alkyl triethylene glycol ether sulfate, and tallow alkyl hexaoxyethylene sulfate. Highly preferred alkyl ether sulfates are those comprising a mixture of individual compounds, said mixture having an average alkyl chain length of from about 12 to about 16 carbon atoms and an average degree of ethoxylation of from about 1 to about 6 moles of ethylene oxide.

Another suitable class of anionic detersive surfactants are the alkyl sulfuric acid salts. Important examples are the salts of an organic sulfuric acid reaction product of a hydrocarbon of the methane series, including iso-, neo-, ineso-, and n-paraffins, having about 8 to about 24 carbon atoms, preferably about 12 to about 18 carbon atoms and a sulfonating agent, e.g., $SO_3$, $H_2SO_4$, oleum, obtained according to known sulfonation methods, including bleaching and hydrolysis. Preferred are alkali metal and ammonium sulfated $C_{12\text{-}38}$ n-paraffins.

Additional examples of synthetic anionic detersive surfactants which come within the terms of the present invention are the olefin sulfonates, the beta-alkyloxy alkane sulfonates, and the reaction products of fatty acids esterified with isethionic acid and neutralized with sodium hydroxide, as well as succinamates. Specific examples of succinamates include disodium N-octadecyl sulfofosuccinamate; tetrasodium N-(1,2-dicarboxyethyl)-N-octadecylsulfosuccinamate; diamyl eater of sodium sulfosuccinic acid; dihexyl ester of sodium sulfosuccinic acid; dioctyl esters of sodium sulfosuccinic acid.

Many additional synthetic anionic surfactants are described in *McCutcheon's. Emulsifiers and Detergents,* 1989 *Annual,* published by M. C. Publishing Co., which is incorporated herein by reference in its entirety. Also V.S. Patent 3,929,678, Laughlin et al., issued Dec. 30, 1975, discloses many other anionic as well as other surfactant types and is incorporated herein by reference in its entirety.

Preferred anionic detersive surfactants for use in the present shampoo compositions include ammonium lauryl sulfate, ammonium laureth sulfate, trlethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, trlethanolamine 1 lauryl sulfate fate, triethanolamine lauryl sulfate, monoethanolamine cocoyl sulfate, monoethanolamine lauryl sulfate, sodium tridecyl benzene sulfonate, and sodium dodecyl benzene sulfonate.

Amphoteric Surfactant

The hair conditioning shampoo composition of the present invention preferably contains an amphoteric detersive surfactants. The amount of this surfactant is preferably no more than about 10 weight %. Examples of amphoteric detersive surfactants which can be used in the compositions of the present invention are those which are broadly described as derivatives of aliphatic secondary and tertiary amines in which the aliphatic substituent contains from about 8 to 18 carbon atoms and one contains an anionic water solubilizing group e.g., carboxy, sulfonate, sulfate, phosphate, or phosphonate. Examples of compounds falling within this definition are sodium 3-dodecylaminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "MIRANOL" as described in U.S. Pat. No. 2,528,378.

Optional Detersive Surfactants

In addition to the anionic detersive surfactant component, the compositions of the present invention can optionally contain other detersive surfactants. These include nonionic surfactants, and zwitterionic surfactants. Optional detersive surfactants, when used, are typically present at levels of from about 0.5% to about 20%, more typically from about 1% to about 10%, although higher or lower levels can be used. The total amount of detersive surfactant in compositions containing optional detersive surfactants in addition to the anionic surfactant will generally be from about 5.5% to about 40%, preferably from about 8% to about 30%, more preferably from about 10% to about 25%. Cationic detersive surfactants can also be used, but are generally less preferred because they can adversely interact with the anionic detersive surfactant. Cationic detersive surfactants, if used, are preferably used at levels no greater than about 5%. Cationic surfactants, if used, are more typically conditioning agents which can optionally be included in the compositions hereof.

Nonionic detersive surfactants which can be used include those broadly defined as compounds produced by the condensation of alkylene oxide groups (hydrophilic in nature) with an organic hydrophobic compound, which may be aliphatic or alkyl aromatic in nature. Examples of preferred classes of nonionic detersive surfactants are: The long chain alkanolamides; the polyethylene oxide condensates of alkyl phenols; the condensation product of aliphatic alcohols having from about 8 to about 18 carbon atoms, in either straight chain or branched chain configuration, with ethylene oxide; the long chain tertiary amine oxides; the long chain tertiary phosphine oxides; the long chain dialkyl sulfoxides containing one short chain alkyl or hydroxy alkyl radical of from about 1 to about 3 carbon atoms; and the alkyl polysaccharide (APS) surfactants such as the alkyl polyglycosides; the polyethylene glycol (PEG) glyceryl fatty esters.

Other zwitterionics such as betaines can also useful in the present invention. Examples of betaines useful herein include the high alkyl betaines, such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the $RCONH(CH_2)_3$ radical is attached to the nitrogen atom of the betaine are also useful in this invention.

Preferred shampoos of the present invention contain combinations of anionic surfactants with zwitterionic surfactants and/or amphoteric surfactants. Especially preferred shampoos contain from about 0% to about 16% of alkyl sulfates, from 0% to about 16% of ethoxylated alkyl sulfates, and from about 0% to about 10% of optional detersive surfactants selected from the nonionic, amphoteric, and zwitterionic detersive surfactants, with at least 5% of either alkyl sulfate, ethoxylated alkyl sulfate, or a mixture thereof, and a total surfactant level of from about 10% to about 25%.

Silicone Hair Conditioning Agent

An essential component of the present invention is a nonvolatile, nonionic silicone hair conditioning agent which is insoluble in the shampoo compositions hereof. The silicone hair conditioning agent is intermixed in the shampoo composition so as to be in the form of dispersed, insoluble particles, or droplets. The silicone hair conditioning agent comprises a nonvolatile, insoluble, silicone fluid and optionally comprises a silicone gum which is insoluble in the shampoo composition as a whole but is soluble in the, silicone fluid. The silicone hair conditioning agent can also comprise other ingredients, such as a silicone resin to enhance deposition efficiency.

The silicone hair conditioning agent may comprise low levels of volatile silicone components; however, such volatile silicones will preferably exceed no more than about 0.5%, by weight, of the shampoo composition. Typically, if volatile silicones are present, it will be incidental to their use as a solvent or carrier far commercially available forms of other ingredients, such as silicone gums and resins The silicone hair conditioning agent for use herein will preferably have viscosity of from about 1,000 to about 2,000,000 centistokes at 25° C., more preferably from about 10,000 to about 1,800,000, even more preferably from about 100,000 to about 1,500,000. The viscosity can be measured by means of a glass capillary viscometer as set forth in Dow Coming Corporate test method CTM0004, Jul. 20, 1970.

The silicone hair conditioning agent will be used in the shampoo compositions hereof at levels of from about 0.5% to about 10% by weight of the composition, preferably from about 0.1% to about 10%, more preferably from about 0.5% to about 8%, most preferably from about 0.5% to about 5%.

Suitable insoluble, nonvolatile silicone fluids include polyalkyl siloxanes, polyaryl siloxanes, polyalkylaryl siloxanes, polyether siloxane copolymers, and mixtures thereof. Other insoluble, nonvolatile silicones fluids having hair conditioning properties can also be used. The term "nonvolatile" as used herein shall mean that the silicone material exhibits very low or no significant vapor pressure at ambient conditions, as is understood by those in the art. The term "silicone fluid" shall mean flowable silicone materials having a viscosity of less than 1,000,000 centistokes at 25° C. Generally, the viscosity of the fluid will be between about 5 and 1,000,000 centistokes at 25° C., preferably between about 10 and about 100,000.

The nonvolatile polyalkylsiloxane fluids that may be used include, for example, polydimethyl siloxanes. These siloxanes are available, for example, from the General Electric Company in their Viscasil® and SF 96 series, and from Dow Corning in their Dow Coming 200 series.

The polyalkylaryl siloxane fluids that may be used, also include, for example, polymethylphenylsiloxanes. These siloxanes are available, for example, from the General Electric Company as SF 1075 methyl phenyl fluid or from Dow Coming as 556 Cosmetic Grade Fluid.

The polyether siloxane copolymers that may be used include, for example, a polypropylene oxide modified polydimethylsiloxane (e.g., Dow Corning DC-1248) although ethylene oxide or mixtures of ethylene oxide and propylene oxide may also be used. The ethylene oxide and polypropylene oxide level must be sufficiently low to prevent solubility in water and the composition hereof.

References disclosing suitable silicone fluids include U.S. Pat. No. 2,826,551, Geen; U.S. Pat. No. 3,964,500, Drakoff, issued Jun. 22, 1976; U.S. Pat. No. 4,364,837, Pader; U.S. Pat. No. 5,573,709, Wells; British Patent 849,433, Woolston; and PCT Patent Application WO93/08787. All of these patents are incorporated herein by reference in their entireties. Also incorporated herein by reference is ,Silicon Compounds distributed by Petrarch Systems, Inc., 1984. This reference provides an extensive (though not exclusive) listing of suitable silicone fluids.

Another silicone material that can be especially useful in the silicone conditioning agents is insoluble silicone gum. The term "silicone gum", as used herein, means polyorganosiloxane materials having a viscosity at 25° C. of greater than or equal to 1,000,000 centistokes. Silicone gums are described by Petrarch and others including U.S. Pat. No. 4,152,416, Spitzer et al., issued May 1, 1979 and Noll, Walter, *Chemistry and Technology of Silicones,* New York: Academic Press 1968. Also describing silicone gums are General Electric Silicone Rubber Product Data Sheets SE 30, SE 33, SE 54 and SE 76. All of these described references are incorporated herein by reference. The "silicone gums" will typically have a mass molecular weight in excess of about 200,000, generally between about 200,000 and about 1,000,000. Specific examples include polydimethylsiloxane, (polydimethyl siloxane) (methylvinylsiloxane) copolymer, poly(dimethyl siloxane) (diphenyl siloxane)(methylvinylsiloxane) copolymer and mixtures thereof.

Preferably the silicone hair conditioning agent comprises a mixture of a polydimethylsiloxane gum, having a viscosity greater than about 1,000,000 centistokes and polydimethyl siloxane fluid having a viscosity of from about 10 centistokes to about 100,000 centistokes, wherein the ratio of gum to fluid is from about 30:70 to about 70:30, preferably from about 40:60 to about 60:40.

Another optional ingredient that can be included in the silicone conditioning agent is silicone resin. Silicone resins are highly crosslinked polymeric siloxane systems. The crosslinking is introduced through the incorporation of trifunctional and tetrafunctional silanes with monofunctional or difunctional, or both, silanes during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units (and hence, a sufficient level of crosslinking) such that they dry down to a rigid, or hard, film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. Preferably, the ratio of oxygen:silicon atoms is at least about 1.2:1.0 Silanes used in the manufacture of silicone resins include monomethyl-, dimethyl-, trimethy-, monophenyl-, diphenyl-, methylphenyl-, monovinyl-, and methylvinyl-chlorosilanes, and tetrachlorosilane, with the methyl-substituted silanes being most commonly utilized. Preferred resins are offered by General Electric as GE SS4230 and SS4267. Commercially available silicones resins will generally be supplied in a dissolved form in a low viscosity volatile or nonvolatile silicone fluid. The silicone resins for use herein should be supplied and incorporated into the present compositions in such dissolved form, as will be readily apparent to those skilled in the art.

Background material on silicones including sections discussing silicone fluids, gums, and resins, as well as manufacture of silicones, can be found in *Encyclopedia of Polymer science and Engineering*, Volume 15, Second Edition, pp.294–308, John Wiley & Sons, Inc., 1989, incorporated herein by reference.

Silicone materials and silicone resins in particular, can conveniently be identified according to a shorthand nomenclature system well known to those skilled in the art as "MDTQ" nomenclature. Under this system, the silicone is described according to presence of various siloxane monomer units which make up the silicone. Briefly, the symbol M denotes the monofunctional unit $(CH_3)_3SiO_{0.5}$; D denotes the difunctional unit $(CH_3)_2SiO$; T denotes the trifunctional unit $(CH_3)SiO_{1.5}$; and Q denotes the quadri- or tetra-functional unit $SiO_2$. Primes of the unit symbols, D', T', and Q' denote substituents other than methyl, and must be specifically defined for each occurrence. Typical alternate substituents include groups such as vinyl, phenyls, amines, hydroxyls, etc. The molar ratios of the various units, either in terms of subscripts to the symbols indicating the total number of each type of unit in the silicone (or an average thereof) or as specifically indicated ratios in combination with molecular weight complete the description of the silicone material under the MDTQ system. Higher relative molar amounts of T, Q, T' and/or Q' to D, D', M and/or or M' in a silicone resin is Indicative of higher levels of crosslinking. As discussed before, however, the overall level of crosslinking can also be indicated by the oxygen to silicon ratio.

The silicone resins for use herein which are preferred are MQ, MT, MTQ, MQ and MDTP resins. Thus, the preferred silicone substituent is methyl. Especially preferred are MQ resins wherein the M:Q ratio is from about 0.5:1.0 to about 1.5:1.0 and the average molecular weight of the resin is from about 1000 to about 10,000.

The weight ratio of the nonvolatile silicone fluid component to the silicone resin component, when used, is from about 4:1 to about 400:1, preferably this ratio is from about 9:1 to about 200:1, more preferably from about 19:1 to about 100:1, particularly when the silicone fluid component is a polydimethyl siloxane fluid or a mixture of polydimethylsiloxane fluid and polydimethylslloxane gum as described above.

Examples of the more preferred silicones used as component (b) include, dimethicone, cyclomethicone, trimethyl silyl amodimethicone, phenyl trimethicone, trimethyl siloxy silicate, polyorganosiloxane, polyalkylsiloxane, polyarylsiloxane, polyalkylarylsiloxane, and polyestersiloxane copolymers.

It has been found that for compositions containing silicone and a conditioning oily liquid (as described below), ampholytic polymer conditioning agents having sufficiently high cationic charge density within the above range can provide enhanced conditioning performance and coacervate formation.

Organic Water Insoluble Liquid

The shampoo compositions of the present invention preferably contains a nonvolatile, water insoluble, organic, oily liquid as a preferred type of hair conditioning agent. The hair conditioning oily liquid can add shine and luster to the hair. Additionally, it can also enhance dry combing and dry hair feel. The hair conditioning oily liquid is typically present in the compositions at a level of from about 0.05% to about 5%, by weight of the composition, preferably from about 0.2% to about 3%, more preferably from about 0.5% to about 1%.

By "nonvolatile" what is meant is that the oily material exhibits very low or no significant vapor pressure at ambient conditions (e.g., 1 atmosphere, 25° C.), as is understood in the art. The nonvolatile oily materials preferably have a boiling point at ambient pressure of about 250° C. or higher.

By "water insoluble" what is meant is that the oily liquid is not soluble in water (distilled or equivalent) at a concentration of 0.1%, at 25° C.

The hair conditioning oily liquids hereof generally will have a viscosity of about 3 million cs or less, preferably about 2 million cs or less, more preferably about 1.5 million cs or less.

The hair conditioning oily materials hereof are liquids selected from the group consisting of hydrocarbon oils and fatty eaters. The fatty esters hereof are characterized by having at least 12 carbon atoms, and include esters with hydrocarbon chains derived from fatty acids or alcohols, e.g., mono-esters, polyhydric alcohol esters, and di- and tri-carboxylic acid esters. The hydrocarbyl radicals of the fatty esters hereof can also include or have covalently bonded thereto other compatible functionalities, such as amides and alkoxy moieties (e.g.,, ethoxy or ether linkages, etc.).

Hydrocarbon oils include cyclic hydrocarbons, straight chain aliphatic hydrocarbons (saturated or unsaturated), and branched chain aliphatic hydrocarbons (saturated or unsaturated). Straight chain hydrocarbon oils will preferably-contain from about 12 to about 19 carbon atoms, although it is not necessarily meant to be limit the hydrocarbons to this range. Branched chain hydrocarbon oils can and typically may contain higher numbers of carbon atoms. Also encompassed herein are polymeric hydrocarbons of alkenyl monomers, such as $C_2$–$C_6$ alkenyl monomers. These polymers can be straight or branched chain polymers. The straight chain polymers will typically be relatively short in length, having a total number of carbon atoms as described above for straight chain hydrocarbons in general The branched chain polymers can have substantially higher chain length. The number average molecular weight of such materials can vary widely but will typically be up to about 500, preferably from about 200 to about 400, more preferably from about 300 to about 350.

Specific examples of suitable materials include paraffin oil, mineral oil, saturated and unsaturated dodecane, saturated and unsaturated tridecane, saturated and unsaturated tetradecane, saturated and unsaturated pentadecane, saturated and unsaturated hexadecane, and mixtures thereof. Branched-chain isomers of these compounds, as well as of higher chain length hydrocarbons, can also be used. Exemplary branched-chain isomers are highly branched saturated or unsaturated alkanes, such as the permethyl-substituted isomers, e.g., the permethyl-substituted isomers of hexadecane and undecane, such as 2,2,4,4,6,6,8,8-dimethyl-10-methylundecane and 2,2,4,4,6,6-dimethyl-8-methylnonane, sold by Permethyl Corporation. A preferred hydrocarbon polymer is polybutene, such as the copolymer of isobutylene and butene. A commercially available material of this type is L-1 9 polybutene from Amoco Chemical Co. (Chicago, Ill., USA)

Monocarboxylic acid esters hereof include esters of alcohols and/or acids of the formula R'COOR wherein alkyl or alkenyl radicals and the sun of carbon atoms in R' and R is at least 10, preferably at least 20

Fatty esters include. for example, alkyl and alkenyl esters of fatty acids having aliphatic chains with from about 10 to about 22 carbon atoms, and alkyl and alkenyl fatty alcohol carboxylic acid esters having an alkyl and/or alkenyl alcohol-derived aliphatic chain with about 10 to about 22 carbon atoms, and combinations thereof. Examples include isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyl decyl adipate, lauryl lactate, myristyl lactate, cetyl lactate, oleyl stearate, oleyl oleate, oleyl myristate, lauryl acetate, cetyl propionate, and oleyl adipate.

The mono-carboxylic acid ester however need not necessarily contain at least one chain with at least 10 carbon atoms, so long as the total number of aliphatic chain carbon atoms is at least 10. Examples include diisopropyl adipate, diisohexyl adipate, and diisopropyl sebacate.

Di- and tri-alkyl and alkenyl esters of carboxylic acids can also be used. These include, for example, esters of $C_4$–$C_8$ dicarboxylic acids such as $C_1$–$C_{22}$ esters (preferably $C_1$–$C_6$) of succinic acid, glutaric acid, adipic acid, hexanoic acid, heptanoic acid, and octanoic acid. Specific examples include isocetyl stearyl stearate, diisopropyl adipate, and tristearyl citrate. Polyhydric alcohol esters include alkylene glycol esters, for and di-fatty acid esters, diethylene example ethylene glycol mono glycol mono- and di-fatty acid esters, polyethylene glycol mono and di-fatty acid esters, propylene glycol mono- and di-fatty acid esters, polypropylene glycol mono oleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, polyoxyethylene sorbitan fatty acid esters are satisfactory polyhydric alcohol esters for use herein.

Glycerides include mono-, di-, and tri-glycerides. More specifically, included are the mono-, di-, and trimesters of glycerol and long chain carboxylic acids, such as $C_1$–$C_{22}$ carboxylic acids. A variety of these types of materials can be obtained from vegetable and animal fats and oils, such as castor oil, safflower oil, cotton seed oil, corn oil, olive oil, cod liver oil, almond oil, avocado oil, palm oil, sesame oil, lanolin and soybean Synthetic oils include triolein and tristearin glyceryl dilaurate. Preferred glycerides are di-, and tri-glycerides. Especially preferred are triglycerides.

Aqueous Carrier

The shampoo compositions of the present invention are typically liquids which, preferably, are pourable at room temperature. The compositions hereof will comprise an aqueous carrier, i.e., water, which will generally be present at a level of about 20% to about 95% by weight of the composition, preferably from about 60% to about 85% for pourable, liquid formulations. The compositions of the present invention can also be in other forms, such as gels, mouse, etc. In such cases, appropriate. components known in the art such as gelling agents (e.g., hydroxyethyl cellulose), etc. can be included in the compositions. Gels will typically contain from about 20% to about 90% water. Mousses will be a low viscosity composition and will be packaged as a sprayable liquid according to techniques well known in the art, typically in an aerosol canister including a propellant or a means for generating an aerosol spray.

Since the silicone conditioning agent used in the present compositions is an insoluble silicone dispersed in the compositions, it is preferred to utilize a suspending agent for the silicone. Suitable suspending agents are long chain acyl derivatives, long chain amine oxides, and mixtures thereof, wherein such suspending agents are present in the shampoo compositions in crystalline form. A variety of such suspending agents are described in U.S. Pat. No. 4,741,855, Grote et al., issued May 3, 1988. Especially preferred is ethylene glycol distearate.

Also included among the long chain acyl derivatives useful as suspending agents are the N,N-di(hydrogenated) $C_8$–$C_{22}$ (preferably $C_{12}$–$C_{22}$, more preferably $C_{16}$–$C_{18}$) amido benzoic acid, or soluble salt (e.g., K, Na salts) thereof particularly N,N-di(hydrogenated)tallow amido benzoic acid which is commercially marketed by Stepan Company (Northfield, Ill., USA).

Another useful suspending agent for the silicone conditioning agents of the present compositions is xanthan gum as described in U.S. Pat. No. 4,788,006, Bolich et al., issued Jun. 5, 1984. The combination of long chain acyl derivatives and xanthan gum as a suspending system for silicone is described in U.S. Pat. No. 4,704,272, Oh et al., issued Nov. 3, 1987, and may also be used in the present compositions.

Generally, the shampoo compositions will comprise from about 0.1% to about 5.0%, preferably from about 0.5% to about 3.0%, of the suspending agent to suspend the silicone conditioning agent.

Optional Components

The present compositions may also comprise a variety non-essential, optional shampoo components suitable for rendering such compositions more cosmetically or aesthetically acceptable or to provide them with additional usage benefits. A variety of such to those skilled in the art, and these ingredients are well-known include without limiting the invention thereto: pearlescent aids, such as coated mica, ethylene glycol distearate; opacifiers, such as Tin,; preservatives, such as 1,2-dibromo-2,4-dicyano butane (MERGUARD, Calgon Corporation, Pittsburgh, Pa., USA), benzyl alcohol, 1,3-bis(hydroxymethyl)-5, 5-dimethyl-2,3-imidazolidinedione (e.g., GLYDANT, Glyco Inc., Greenwich, Conn., USA), methylchloroisothiazolinone (e.g., Kathon, Rohm & Haas Co., Philadelphia, Pa., USA), methyl paraben, propyl paraben, and imidazolidinyl urea; fatty alcohols, such as cetearyl alcohol, cetyl alcohol, and stearyl alcohol; sodium chloride; amnonium chloride; sodium sulfate; ethyl alcohol; pH adjusting aids, such as citric acid, sodium citrate, succinic acid, phosphoric acid, monosodium phosphate, disodium phosphate, sodium hydroxide, and sodium carbonate; coloring agents or dyes; perfumes; and sequestering agents, such as disodium ethylenediamine tetra-acetate (EDTA).

Another optional ingredient that can be advantageously used is an anti-static agent. The anti-static agent should not unduly interfere with the in-use performance and end-benefits of the shampoo; particularly, the anti-static agent should not interfere with the anionic detersive surfactant. Suitable anti-static agents include, for example, tricetyl methyl amnonium chloride.

Typically, from about 0.1% to about 5%; of such anti-static agent is incorporated into the shampoo compositions.

Though the silicone suspending agent component may act to thicken the present compositions to some degree, the present compositions may also optionally contain other thickeners and viscosity modifiers such as an ethanolamide of a long chain fatty acid, such as polyethylene (3) glycol lauramide and coconut monoethanolamide (cocamide MEA) and ammonium xylene sulfonate.

These optional components generally are used individually in the compositions of the present invention at a level of from about 0.01% to about 10%, preferably from about 0.05% to about 5.0% of the shampoo composition.

Method of Manufacture

The compositions of the present invention, in general, can be made by mixing the materials together at elevated temperature, e.g., about 72° C. The silicones resin, if any, and silicone fluid component are first mixed together before being mixed with the other ingredients. The other ingredients are added and the complete mixture is mixed thoroughly at the elevated temperature and is then pumped through a high shear mill and then through a heat exchanger to cool it to ambient temperature. A portion of the liquid components or soluble components (including, for example, ampholytic polymer conditioning agent) can be added to the composition after cooling the mix of surfactants and solids.

Method of Use

The shampoo compositions of the present invention are utilized conventionally, i.e., the hair is shampooed by applying an effective amount of the shampoo composition to the scalp, and then rinsing it out with water. Application of the shampoo to the scalp in general, encompasses messaging or working the shampoo in the hair such that all or most of the hair on the scalp is contacted. The term an "effective amount" as used herein, is an amount which is effective in cleaning and conditioning the hair. Generally, from about 1 g to about 20 g of the composition is applied for cleaning and conditioning the hair. preferably, the shampoo is applied to hair in a wet or damp state.

The compositions hereof can also be useful for cleaning and conditioning the skin. For such applications, the composition would be applied to the skin in a conventional manner, such as by rubbing or massaging the skin with the composition, optionally in the presence of water, and then rinsing it away with water.

EXAMPLES

The following examples illustrate the present invention. It will be appreciated that other modifications of the present invention within the skill of those in the hair care formulation art can be undertaken without departing from the spirit and scope of this s invention.

All parts, percentages, and ratios herein are by weight unless otherwise specified. Some components may came from suppliers as dilute solutions. The levels given reflect the weight percent of the active material, unless otherwise specified.

The following Example 1 is a shampoo composition of the present invention.

Example 1

| | Ingredient | INCI Name | % W/W |
|---|---|---|---|
| Part A | Water | Water | q.s. to 100 |
| | MERQUAT 2001[1] | Polyquaternium-47 | 1.3 |
| Part B | Silicone SF1214 GE[2] | Dimethicone (and) Cyclomethicone | 1.0 |
| | Standapol A[3] | Ammonium Lauryl Sulfate | 46.0 |
| Part | Stearic Acid | Stearic Acid | 1.3 |
| C | Hampene Na2[4] | Disodium EDTA | 0.15 |
| | Aminol CM[5] Fintex | Cocamide MEA | 1.3 |
| | EGDS | Ethylene Glycol Distrearate | 1.0 |
| | MERGUARD[1] 1200 | Methyldibromo Glutaronitrile (and) Phenoxyethanol | 0.15 |
| | Amm. Hydroxide | Ammonium Hydroxide | q.s. to pH 6.5 |
| | Amm. Chloride | Ammonium Chloride | q.s. for Visc. |

This composition of Example 1 exhibited excellent wet combing properties, as detailed in Example 4.

[1] From Calgon Corporation
[2] From GE Silicones
[3] From Henkel
[4] From Hampshire
[5] From Finetex

Example 2

This Example 2 is a comparative shampoo composition that has all the ingredients of Example 1 except silicone.

| | Ingredient | INCI Name | % W/W |
|---|---|---|---|
| Part A | Water | Water | q.s. to 100 |
| | MERQUAT 2001 | Polyquaternium-47 | 1.3 |
| Part B | Standapol A | Ammonium Lauryl Sulfate | 46.0 |
| Part | Stearic Acid | Stearic Acid | 1.3 |
| C | Hampene Na2 | Disodium EDTA | 0.15 |
| | Aminol CM | Cocamide MEA | 1.3 |
| | EGDS | Ethylene Glycol Distrearate | 1.0 |
| | MERGUARD 1200 | Methyldibromo Glutaronitrile (and) Phenoxyethanol | 0.15 |
| | Amm. Hydroxide Ammonium | Ammonium Hydroxide | q.s. to pH 6.5 |

This composition did not condition the hair as well as Example 1. This is illustrated in Example 4, showing that it required more work to comb the experimental hair tresses treated with the shampoo composition of this example than that of Example 1.

Example 3

This Example 3 is a shampoo composition that is also a comparison example as it contained all of the ingredients of Example 1 except the ampholytic polymer.

| | Ingredient | INCI Name | % W/W |
|---|---|---|---|
| Part A | Water | Water | q.s. to 100 |
| Part B | Silicone SF1214 GE | Dimethicone (and) Cyclomethicone | 1.0 |
| | Standapol A | Ammonium Lauryl Sulfate | 46.0 |
| Part C | Stearic Acid | Stearic Acid | 1.3 |
| | Hampene Na2 | Disodium EDTA | 0.15 |
| | Aminol CM | Cocamide MEA | 1.3 |

-continued

| Ingredient | INCI Name | % W/W |
|---|---|---|
| EGDS | Ethylene Glycol Distrearate | 1.0 |
| MERGUARD 1200 | Methyldibromo Glutaronitrile (and) Phenoxyethanol | 0.15 |
| Amm. Hydroxide | Ammonium Hydroxide | q.s. to pH 6.5 |
| Amm. Chloride | Ammonium Chloride | q.s. for Visc. |

This composition did not condition the hair as well as Example 1. This is also illustrated in Example 4, showing that it required more work to comb the experimental hair tresses treated with the shampoo composition of this example than that of Example 1.

Example 4

This Example 4 is a combination of the prior three examples, illustrating the "Wet Hair Combability" of hair treated with the shampoo compositions of Examples 1–3.

The shampoos from Examples 1–3 were evaluated for wet hair combing using the Dia-Stron Mini Tensile Tester, Dia-Stron Limited, Andover, Hampshire, U.K. The amount of work (mj) required to comb the hair is measured directly. Lower work levels indicate superior conditioning as the hair is easier to comb.

| Shampoo | Total Work (mj) |
|---|---|
| Example 1 | 27.7 |
| Example 2 | 46.7 |
| Example 3 | 54.1 |

What is claimed is:

1. A hair conditioning shampoo composition comprising:
   (a) about 5% to about 50%, by weight, of a surfactant component selected from the group consisting of anionic surfactants and amphoteric surfactants;
   (b) about 0.05% to about 10%, by weight, of a dispersed, insoluble, nonionic silicone hair conditioning agent;
   (c) about 0.05% to about 10%, by weight, of a water soluble, organic, ampholytic polymer hair conditioning agent; and
   (d) an aqueous carrier
wherein said ampholytic polymer hair conditioning agent of (c) is comprised of at least one ethylenically unsaturated cationic monomer and at least one ethylenically unsaturated acid containing monomer.

2. The hair conditioning shampoo composition of claim 1 wherein component (a) is in a concentration of about 5% to about 25% by weight.

3. The hair conditioning shampoo composition according to claim 1 wherein the surfactant component of (a) is anionic.

4. The hair conditioning shampoo composition according to claim 2 wherein the composition contains both anionic and nonionic surfactants.

5. The hair conditioning shampoo composition according to claim 1 wherein the surfactant component (a) is present in a concentration of about 5% to about 25% by weight, the silicone hair conditioning agent (b) is present in a concentration of about 0.1% to about 7%, by weight, and the ampholytic polymer hair conditioning agent (c) is present in a concentration of about 0.1% to about 4%, by weight, all in an aqueous (d).

6. The hair conditioning shampoo composition according to claim 5 wherein the surfactant component (a) is present in a concentration of about 10% to about 20% weight, the silicone hair conditioning agent (b) is present in a concentration of about 0.5% to about 5% by weight, and the ampholytic polymer hair conditioning agent (c) is present in a concentration of about 0.1% to about 3%, by weight.

7. The hair conditioning shampoo according to claim 1 wherein said ampholytic hair conditioning polymer is comprised of:
   (A) about 1 to about 99 mol % of methacrylamidopropyltrimethyl ammonium chloride;
   (B) about 1 to about 99 mol % of acrylic acid;
   (c) about 1 to about 40 mol % of methacrylate.

8. The hair conditioning shampoo composition according to claim 7 wherein the mol ratio of (A):(B) in said ampholytic polymer hair conditioning agent ranges from about 25:75 to about 75:25.

9. The hair conditioning shampoo composition according to claim 7 wherein the mol ratio ratio (A):(B) of 25:75 to 75:25, (C) is present in an amount of about 1 to about 35 mol %.

10. The hair conditioning shampoo composition according to claim 9 wherein said ampholytic polymer hair conditioning agent is selected from the group of polymers consisting of (1) a polymer comprised of about 45 mol %, methacrylamidopropyltrimethyl ammonium chloride, about 45 mol % acrylic acid, and about 10 mol % methylacrylate.

11. The hair conditioning shampoo composition according to claim 1 further comprising a suspending agent for said silicone hair conditioning agent and about 0.05 to about 5% by weight of an organic water insoluble liquid selected from the group consisting of hydrocarbon oils, fatty esters having 10 to 22 carbon atoms, and mixtures thereof.

12. The hair conditioning shampoo composition according to claim 1 wherein said ampholytic polymer hair conditioning agent exists in a complex coacervate form upon dilution of the components (a), (b), and (c) with water at a water:shampoo composition weight ratio of 20:1.

13. A method for treating hair comprising contacting hair with the composition of claim 1.

14. A method for treating hair comprising contacting hair with the composition of claim 10 wherein (a) contains 15 weight % anionic surfactant and about 1 to 2 weight % nonionic surfactant, (b) contains about 0.5 to 1.5% silicone, and (c) contains about 0.2 to 0.4 weight percent of said ampholytic polymer hair conditioning agent.

15. The composition according to claim 14 wherein said anionic surfactant of (a) is selected from the group consisting of lauryl sulfate, lauryl ether sulfate, $\alpha$-olefin sulfonates, and their ammonium, sodium and amine salts; said nonionic surfactant of (a) is selected from the group consisting of fatty di or mono ethanol amides, mono or di fatty esters of polyethylene or polypropylene glycol, and mono or di fatty esters of $C_1$–$C_6$ glycols; and the silicone of (b) is selected from the group consisting of dimethicone, cyclomethicone, trimethyl silyl amodimethicone, phenyl trimethicone, trimethyl siloxy silicate, polyorganosiloxane, polyalkylsiloxane, polyarylsiloxane, polyalkarylsiloxane, and polyestersiloxane copolymers.

* * * * *